(12) United States Patent
Schumacher

(10) Patent No.: US 7,717,942 B2
(45) Date of Patent: May 18, 2010

(54) BONE SCREW AND OSTEOSYNTHESIS DEVICE

(75) Inventor: Joerg Schumacher, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1004 days.

(21) Appl. No.: 11/138,771

(22) Filed: May 26, 2005

(65) Prior Publication Data

US 2005/0273101 A1 Dec. 8, 2005

(30) Foreign Application Priority Data

May 28, 2004 (DE) ........................ 10 2004 027 881

(51) Int. Cl.
*A61B 17/70* (2006.01)
*A61B 17/86* (2006.01)

(52) U.S. Cl. .................. 606/266; 606/270; 606/275; 606/304; 606/309; 606/315; 606/319

(58) Field of Classification Search ........... 606/60–279, 606/300–321; 411/384–385, 396–397
See application file for complete search history.

(56) References Cited

U.S. PATENT DOCUMENTS

| | | | | |
|---|---|---|---|---|
| 5,443,467 A | * | 8/1995 | Biedermann et al. | ........ 606/308 |
| 5,569,251 A | * | 10/1996 | Baker et al. | ................. 606/281 |
| 5,752,957 A | * | 5/1998 | Ralph et al. | ................. 606/266 |
| 5,810,817 A | * | 9/1998 | Roussouly et al. | .......... 606/250 |
| 6,146,383 A | | 11/2000 | Studer et al. | |
| 6,206,879 B1 | | 3/2001 | Marnay et al. | |
| 6,663,635 B2 | | 12/2003 | Frigg et al. | |
| 6,835,196 B2 | | 12/2004 | Biedermann et al. | |

(Continued)

FOREIGN PATENT DOCUMENTS

EP   0 938 872   9/1999

(Continued)

OTHER PUBLICATIONS

Leaflet of AESCULAP AG & Co. KG, MACS TL—Thoracic Extension, 2 pages, undated.

(Continued)

*Primary Examiner*—Eduardo C Robert
*Assistant Examiner*—Julianna N Harvey
(74) *Attorney, Agent, or Firm*—Lipsitz & McAllister, LLC

(57) ABSTRACT

In order, even in the case of bone screws with a particularly small head, to ensure a secure hold of the bone screw in a bone, a bone screw is proposed, having a screw body, which defines a longitudinal axis and is provided with a screw body external thread and has a proximal and a distal end, having a coupling element disposed on the proximal end for detachably connecting the screw body to a screw head designed substantially in the form of a U-shaped fork head with a coupling opening, wherein an edge of the coupling opening forms an axial stop for the coupling element for limiting a movement of the coupling element relative to the screw head in distal direction, wherein a maximum outside diameter of the screw body is larger than an inside diameter of the coupling opening, wherein the screw body comprises at least a first and a second screw body part. An osteosynthesis device having such a bone screw and a method of manufacturing such a bone screw are further proposed.

37 Claims, 2 Drawing Sheets

U.S. PATENT DOCUMENTS

2001/0049530 A1* 12/2001 Culbert et al. ................. 606/72
2003/0187439 A1* 10/2003 Biedermann et al. .......... 606/61
2003/0199873 A1   10/2003 Richelsoph

FOREIGN PATENT DOCUMENTS

EP          1 191 891        4/2002
WO          02/076314        10/2002

OTHER PUBLICATIONS

Leaflet of AESCULAP AG & Co. KG, MACS TL—Polyaxial Screw XL, 2 pages, undated.

* cited by examiner

BONE SCREW AND OSTEOSYNTHESIS DEVICE

BACKGROUND OF THE INVENTION

The present invention relates to a bone screw for screwing into a bone. The present invention further relates to an osteosynthesis device for fixing at least two bone parts relative to one another in a fixation position, comprising at least two bone screws and a carrier element fastenable to at least two of the at least two bone screws. The present invention further relates to a method of manufacturing a bone screw.

Known internal fixation devices comprise bone screws that usually carry a screw head, to which a carrier element is fastenable. Such internal fixation devices are used, for example, to fasten two vertebrae of a human spinal column relative to one another, either because an adjacent vertebra is damaged or because a disk connecting the two vertebrae is damaged. In order to ensure as good a hold of the bone screw in the bone as possible, preferably bone screws with as large an external thread diameter as possible are used.

Bone screws are further known, which have a screw head that is movable relative to the screw body of the bone screw. The screw head may be, for example, polyaxially pivotable. In this case, the bone screw cannot be manufactured in one piece but is composed of substantially two parts, namely the screw body and the screw head. For connecting the two parts, in known bone screws the screw head is passed through an opening of the screw head. A maximum outside diameter of the screw body is therefore defined by the inside diameter of the opening.

As the screw head generally projects from the bone, it is desirable to provide particularly small screw heads. However, the size of the screw bodies to be connected to the screw heads may be reduced only to a qualified extent because otherwise it is impossible to guarantee a secure hold of the screw body in the bone.

SUMMARY OF THE INVENTION

The object of the present invention is therefore to improve a bone screw comprising a screw body and a screw head, an osteosynthesis device of the initially described type and a method of manufacturing a bone screw in such a way that, even given particularly small screw heads, a secure hold of the screw body in the bone is guaranteed.

This object is achieved according to the invention by a bone screw, having a screw body, which defines a longitudinal axis, is provided with a screw body external thread and has a proximal and a distal end, having a coupling element disposed on the proximal end for detachably connecting the screw body to a screw head designed substantially in the form of a U-shaped fork head with a coupling opening, wherein an edge of the coupling opening forms an axial stop for the coupling element for limiting a movement of the coupling element relative to the screw head in distal direction, wherein a maximum outside diameter of the screw body is larger than an inside diameter of the coupling opening, wherein the screw body comprises at least a first and second screw body part, which are detachably connectable to one another, wherein the coupling element is disposed on a proximal end of the first screw body part and the second screw body part carries the external thread of the screw body, wherein the first screw body part comprises a first connection element for the detachable connection to a second connection element disposed on the second screw body part and wherein the first screw body part has a distal end, which can be introduced in distal direction through the coupling opening and comprises the first connection element.

The bone screw according to the invention makes it possible to design a screw body of any desired size that in any case guarantees a secure hold in the bone. The screw head may be designed independently of the configuration of the screw body. This means that the coupling opening of the screw head may in particular have an inside diameter that is smaller than a maximum outside diameter of the screw body provided with an external thread. Thus, because the screw body is composed of at least two parts, it is merely necessary to ensure that one of the two screw body parts can be introduced by its distal end through the coupling opening. For assembly, the first screw body part may then be passed by its distal end through the coupling opening until the coupling element disposed on the first screw body part abuts on the edge of the coupling opening that forms an axial stop. In a next step, the two screw body parts may then be connected to one another. This has the added advantage that, particularly in the case of screw bodies having a maximum outside diameter larger than the inside diameter of the coupling opening, a movement of the screw body relative to the screw head in proximal direction is likewise limited. After connection of the two screw body parts in the described manner, it is further ensured that the screw head does not accidentally detach from the screw body. As a result, the handling ability during a surgical intervention is moreover substantially improved.

It is advantageous when the screw head and the coupling element in a connection position, in which the screw head is connected to the screw body, are connected to one another in articulated manner. In this way, the screw head is alignable in a desired manner relative to the screw body, in particular the longitudinal axes of screw head and screw body may be aligned in a desired manner relative to one another. This is particularly helpful if a carrier element of an internal fixation device is to be inserted into the fork head and fixed. The screw body may then be screwed in such a way into the bone that it has an optimum hold and subsequently the screw head may be adjusted relative to the screw body in such a way that the carrier element may be aligned in a desired manner.

Polyaxial adjustability arises in an advantageous manner when the coupling element is of a spherical design. What is more, the portions or regions of the screw head that lie adjacent to the coupling element may also be of a corresponding design to the spherical coupling element in order to form a ball-and-socket joint.

In principle, it would be conceivable to connect the two screw body parts to one another by means of a bayonet joint. However, it is particularly advantageous when the one connection element comprises an internal thread, when the other connection element comprises an external thread corresponding to the internal thread, and when the internal thread and the external thread are disposed coaxially with the longitudinal axis of the screw body. This design allows the bone screw to be anchored also by a minimally invasive surgical procedure in the body of a human or an animal. For example, the second screw body part, which carries the external thread of the screw body, may be screwed into the bone. Then, the first screw body part together with the screw head may easily be screw-fastened to the second screw body part.

A particularly secure connection of the two screw body parts is achieved when the internal thread and the external thread are fine-pitch threads.

To prevent sliding of the coupling element through the coupling opening, it is advantageous when the coupling opening has an inside diameter that is smaller than an outside diameter of the coupling element.

According to a preferred form of construction of the invention, it may be provided that the fork head comprises a connection element receiver, which is delimited by two limbs projecting in proximal direction, and that a carrier element of an osteosynthesis device for connecting two bone screws is insertable into the connection element receiver and fastenable in the connection element receiver. Such a design facilitates the insertion of the carrier element into the connection element receiver. A movement of the carrier element relative to the screw head transversely of a direction defined by the screw head longitudinal axis is moreover prevented.

For insertion of the carrier element into the fork head it is advantageous when the two limbs of the fork head are as long as possible. However, this conflicts with the desire to design as small a screw head as possible. It is therefore advantageous when at least one of the two limbs of the fork head has a predetermined breaking point. After fastening of the carrier element to the fork head, the predetermined breaking point, which may for example be designed in the form of a groove opened in radial direction, makes it possible to reduce the size of the limb in a defined manner, namely, for example, by breaking off the limb of the fork head at the predetermined breaking point. For this purpose, a special instrument may also be provided.

A particularly simple construction of the fork head arises when it is formed by an elongate fork head sleeve, which starting from its proximal end is provided with two diametrically opposed slots forming the connection element receiver, so that a distal end of the fork head is designed in the form of an annular sleeve portion that comprises the coupling opening. Such a screw head, which is also known as a tulip head, ensures that the screw head cannot be detached from the coupling element provided that an outside diameter of the coupling element is larger than an inside diameter of the coupling opening.

It is advantageous when at least one fixing means is provided for fastening the carrier element in the connection element receiver. By means of the at least one fixing means the carrier element, which in a feed position is movable relative to the screw head, is fastenable immovably to the screw head.

The fixing means may be fastened particularly easily to the screw head when the fixing means is screw-fastenable to the screw head.

According to a further preferred form of construction of the invention, it may be provided that the fork head has a fork head thread and that the fixing means has a fixing means thread corresponding to the fork head thread.

It is particularly advantageous when the fixing means thread is an internal thread and the fork head thread is an external thread. For example, the fixing means may be an internally threaded ring that is capable, on the one hand, of fixing the carrier element in the connection element receiver and, on the other hand, of increasing the stability of the limbs projecting in proximal direction because it prevents a rotation of the limbs in a radially outward direction.

In order to design the screw head with fixing means, as a whole, as small as possible, it is advantageous when the fixing means thread is an external thread and the fork head thread is an internal thread. It is therefore possible for the fixing means to be, as it were, countersunk in the screw head.

The construction of the bone screw is particularly simplified when the fixing means thread and the fork head thread are formed coaxially with a screw head longitudinal axis.

So that the two screw body parts may be connected easily to one another, it is advantageous when the first screw body part carries a first tool element receiver for a tool [for connecting] the first screw body part to the second screw body part. For example, the second screw body part may be screwed directly into the bone and then the first screw body part may be connected to the second screw body part by means of a tool introduced into the first tool element receiver.

The first tool element receiver is particularly easily accessible when it is disposed facing in proximal direction on the coupling element. This allows the first screw body part to be introduced into the body of a patient and connected to the second screw body part through minimally invasive access.

In principle, there are various possible ways of designing the tool element receiver. The first tool element receiver is, however, advantageously designed in the form of a slot or an internal or external polygon.

The screw body part advantageously carries a second tool element receiver for a screw-in tool for screwing the second screw body part into the bone. By means of the second tool element receiver the second screw body part may be anchored in the bone independently of the first screw body part. What is more, by said means the second screw body part is also easily detachable from the bone, should the connection of the two screw body parts have come apart and the screw body as a whole not be removable from the bone by means of the first tool element receiver. In particular, it is advantageous to dispose the tool element receiver coaxially with the longitudinal axis of the screw body and facing in proximal direction.

In order to achieve as compact a construction of the bone screw as possible, the second tool element receiver is provided adjacent to the connection element disposed on the second tool element. For example, the connection element may be a blind hole provided with an internal thread, in which case the tool element receiver may be formed either at the proximal end or at the distal end of the threaded portion of the blind hole.

In principle, it would be possible to design the bone screw in such a way that the carrier element is held by means of a fixing element directly against the coupling element disposed on the screw body. In order, however, to achieve as good an adaptation to the shape of the coupling element as possible, it is advantageous if a clamping body supported movably on the fork head is provided and if the clamping body can be held against the coupling element. The introduction of force for fixing the carrier element then occurs from the fixing element via the carrier element to the clamping body and then onto the coupling element. In said case, it is in particular possible to form the clamping body in a corresponding manner to the coupling element so that as great a surface contact as possible is achieved between the clamping body and the coupling element.

It is advantageous when a locking device is provided for detachably connecting the clamping body to the screw head. It is therefore possible, for example, for a very small clamping body to be disposed securely on the screw head. The locking device may comprise, for example, a snap connection or detent connection, by means of which the clamping body is connectable detachably to the screw head.

So that the bone screw in conjunction with an osteosynthesis device may be combined in an advantageous manner, it is advantageous when a carrier element of an internal fixation device for connecting two bone screws can be inserted into the connection element receiver and fastened held between the fixing element and the clamping body.

A particularly simple construction of the bone screw is achieved when the carrier element is of a rod-shaped design.

The connection element receiver may then be designed in a corresponding manner to the external shape of the carrier element.

In order to guarantee a defined connection of the two screw body parts to one another, it is advantageous when the first screw body part has a stop, on which the second screw body part abuts when the two screw body parts are connected to one another.

Manufacture of the bone screw is particularly easy when the stop is designed in the form of a radially projecting annular flange.

In order to increase the stability of the screw body of the bone screw as a whole, it is advantageous when a distance of the distal end of the first screw body part from the stop corresponds at most to 0.4 times a total length of the second screw body part. For one form of construction of the present invention this may mean in particular that, for example, the second screw body part has an internally threaded receiver, which forms the second connection element and the length of which corresponds approximately to 0.4 times the total length of the second screw body part. In other words, this means that approximately 60% of the total length of the second screw body part may be of a solid design. In principle, it would however also be conceivable to provide the screw body with a central through-channel.

It may advantageously be provided that the screw head defines a screw head longitudinal axis and that a plane of symmetry of the connection element receiver contains the screw head longitudinal axis. This symmetrical construction of the screw head considerably simplifies the manufacture thereof. Furthermore, forces acting upon the bone screw may be taken up in an optimum manner.

The stability of the bone screw and its ability to be introduced into a bone are additionally enhanced when the screw body has a core, which comprises at least one cylindrical and two conical portions. The conical portions preferably taper in the direction of the distal end of the screw body.

According to a preferred form of construction of the invention, it may be provided that a first conical portion of the core adjoins the proximal end of the screw body, that the first conical portion merges into a second conical portion, that the second conical portion merges into a cylindrical portion and that the cylindrical portion merges into a screw body point. Preferably, all of the conical portions taper in the direction of the distal end of the screw body.

In order to increase the stability of the screw body, it may advantageously be provided that the first and the second connection element have a diameter corresponding at most to 0.7 times the mean diameter of a core of the screw body in a portion of the screw body, in which one of the two connection elements is provided. It is thereby ensured that, particularly given a form of construction, in which the connection element is in the form of a recess coaxial with the longitudinal axis of the screw body, a wall thickness of the screw body has a minimum thickness.

In order to increase the hold of the bone screw in a bone, it may advantageously be provided that an outside diameter of the external thread of the screw body is constant over at least half of the length of the screw body. Particularly in the case of a conically tapering core, this means that the height of a thread cutting edge of the external thread of the screw body increases in radial direction from the proximal end of the screw body in the direction of the distal end.

It is advantageous when the first and the second screw body part are connected to one another with a defined tightening torque. The defined tightening torque preferably lies in a range of 5 to 20 Nm. By defining a tightening torque that is preferably greater than a release torque for removing the bone screw from a bone, it is ensured that the screw body as a whole may be removed from the bone. In other words, it is possible to prevent the first screw body part from separating from the second screw body part during removal of the bone screw from the bone.

Particularly simple to manufacture, wherein at the same time a secure connection of the two screw body parts to one another is guaranteed, may be achieved when the tightening torque is approximately 10 Nm.

Since preferred forms of construction of the invention provide a cavity that is formed when the first and the second screw body part are connected to one another, it is advantageous when the screw head and the first and the second screw body part are connected under clean-room conditions. In this way, it may be ensured that no impurities pass into the cavity.

To avoid introducing germs into the body of a patient, it is advantageous when, after the connecting of screw head and first and second screw body part, the bone screw is sterilized. In this way, particularly in forms of construction, in which a cavity of the type described above is formed by the connection of the two screw body parts to one another, even germs and impurities contained in the cavity may be rendered harmless.

In a preferred form of construction of the invention, it may be provided that the bone screw is sterilized by exposure to γ-radiation. By virtue of this form of sterilization it may be ensured that, even in the case of a completely sealed cavity that contains germs or impurities, full sterilization of the bone screw is achieved internally and externally. This in particular ensures that, if the two screw body parts accidentally separate from one another, e.g. during removal of the bone screw or as a result of loosening under dynamic load, the bone screw does not have any non-sterile areas that may come into contact with the body of the patient.

The initially stated object is further achieved by an osteosynthesis device of the initially described type according to the invention in that at least one of the at least two bone screws of the internal fixation device is one of the bone screws described above.

In particular, providing one of the previously described bone screws according to the invention in an osteosynthesis device has the advantage of enabling the use of bone screws with a large outside diameter of the screw body, but with a very small screw head. Above all, in the case of operations on the spinal column in the posterior region, screw heads obtrude only to a minimal extent when the entire screw body is anchored in the vertebra.

It is advantageous when the osteosynthesis device comprises at least one bone screw, which has an integrally formed screw body with an outside diameter that is smaller than an inside diameter of a coupling opening of a screw head connectable to the screw body, so that for assembly of the bone screw the screw body is introducible in distal direction through the coupling opening. Such a bone screw is substantially easier and hence less expensive to manufacture. In addition, the stability of such a bone screw given an identical outside diameter of the screw body is greater than a bone screw comprising two screw body parts. In any case, it is advantageous to provide a set of different types of bone screw for the osteosynthesis device in order to be able to take optimum account of all possible indications.

For an optimum introduction of force from the carrier element into the screw body of the bone screw, it is advantageous when the carrier element fixed in the connection element receiver completely overlaps the coupling opening in axial direction. For example, the carrier element may be disposed transversely of the longitudinal axis of the screw head in the connection element receiver and in said case fully covers the coupling opening. This additionally enables a compact construction of the bone screw because, in said case, the carrier element may be disposed centrally above the longitudinal axis of the screw head and, occasionally, also above the longitudinal axis of the screw body.

The initially stated object is further achieved by a method of manufacturing a bone screw comprising the steps:

bringing together the screw head and the first screw body part;

connecting the first screw body part to the second screw body part and tightening the connection of the first screw body part to the second screw body part with the defined tightening torque.

The manufacturing method according to the invention ensures that the two screw body parts cannot accidentally detach from one another. In particular, there is namely the risk that, after implantation of the bone screw, a loosening of the connection of the two screw body parts may occur under dynamic load. This is reliably prevented in this way.

It is particularly advantageous when the tightening torque is defined in a range of 5 to 20 Nm. This, on the one hand, prevents the screw body parts from being able to detach from one another under dynamic load and, on the other hand, achieves the effect, in the case of an explantation of the bone screw during which, for example, forces for removing the bone screw are applied to the first screw body part, that the two screw body parts do not detach from one another. The tightening torque is preferably approximately 10 Nm.

In order to prevent the introduction of germs or impurities into the body of a patient, it is advantageous when the first and the second screw body part of the bone screw are assembled under clean-room conditions. In this way, particularly in the case of bone screws that form a cavity after assembly of the two screw body parts, the number of germs and impurities contained in the cavity may be minimized.

It is further advantageous when, after assembly of the screw head, the first and the second screw body part, the bone screw is sterilized. In this way, it is possible to kill any germs and bacteria that are situated on the inner and/or outer surfaces of the bone screw. Preferably, the bone screw is sterilized by exposure to γ-radiation. γ-radiation is easily capable of penetrating even bone screws made of metal and killing germs and bacteria contained in particular in cavities of the bone screw.

BRIEF DESCRIPTION OF THE DRAWINGS

The following description of a preferred form of construction of the invention in conjunction with the drawings [serves] to provide a detailed explanation.

The drawings show.

DETAILED DESCRIPTION OF THE DRAWINGS

Figure 1:
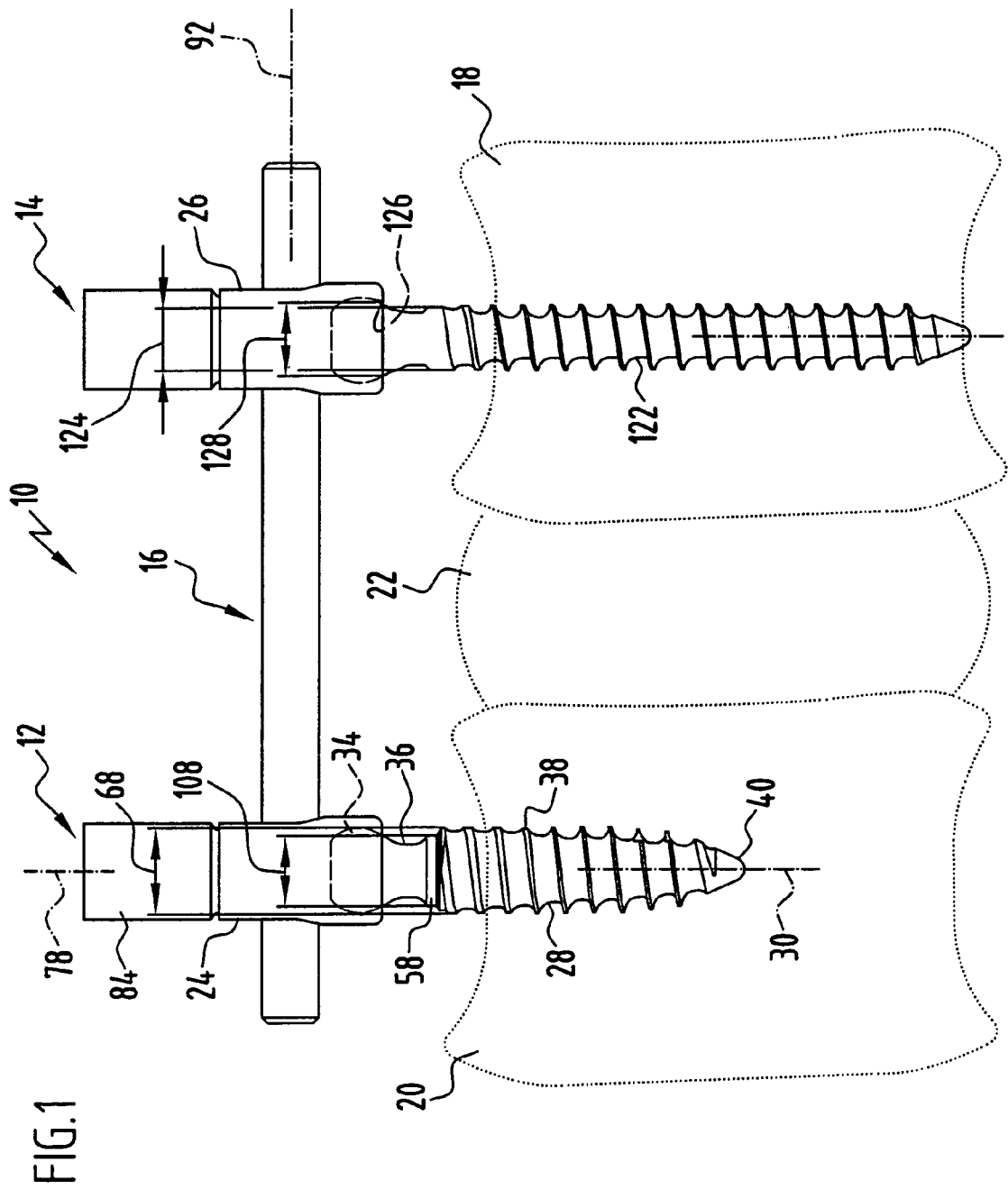
FIG. 1: a side view of an osteosynthesis device according to the invention.

FIG. 1 shows an osteosynthesis device, which is provided as a whole with the reference character 10 and which in the explicitly illustrated case comprises a first bone screw 12 according to the invention, a second bone screw 14 known from the background art and an elongate cylindrical round rod 16 serving as a carrier element. The osteosynthesis device 10 may further comprise non-illustrated bone screws of another type, in particular bone screws, to which a plurality of round rods or bone plates are fastenable. In addition, a plurality of round rods 16 may be provided.

The osteosynthesis device 10 may be used in particular to fasten two vertebrae 18 and 20, which are illustrated diagrammatically and by dotted lines in FIG. 1, at a desired spacing from one another, e.g. when a disk 22 disposed between the two vertebral bodies 18 and 20 and likewise illustrated by dotted lines in FIG. 1 is damaged. In said case, a bone screw is screwed into each of the two vertebral bodies 18 and 20, e.g. the bone screw 14 into the vertebral body 18 and the bone screw 12 into the vertebral body 20. Each of the two bone screws 12 and 14 has a screw head 24 and 26 respectively, to which the round rod 26 is fixable. As the screw heads 24 and 26 are identical in construction, in connection with a detailed description of the screw 12 the screw head 24 is described in detail below by way of example also for the screw head 26.

Figure 2:
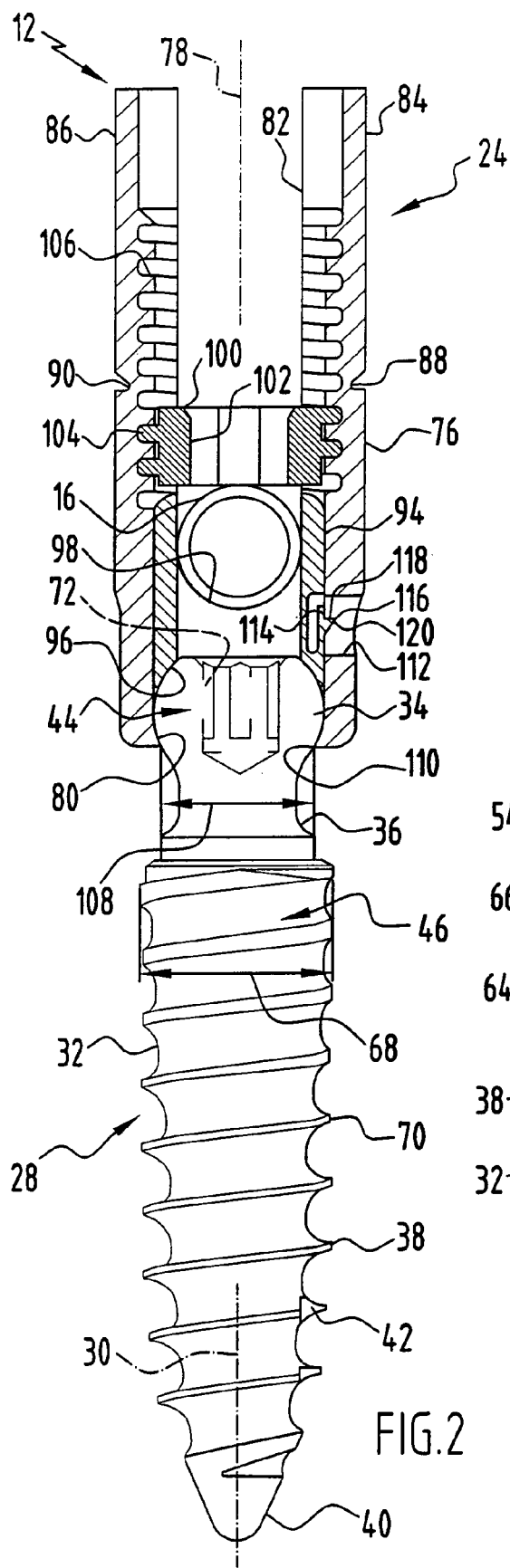
FIG. 2: a part-sectional side view of the bone screw illustrated on the left in FIG. 1.
Figure 3:
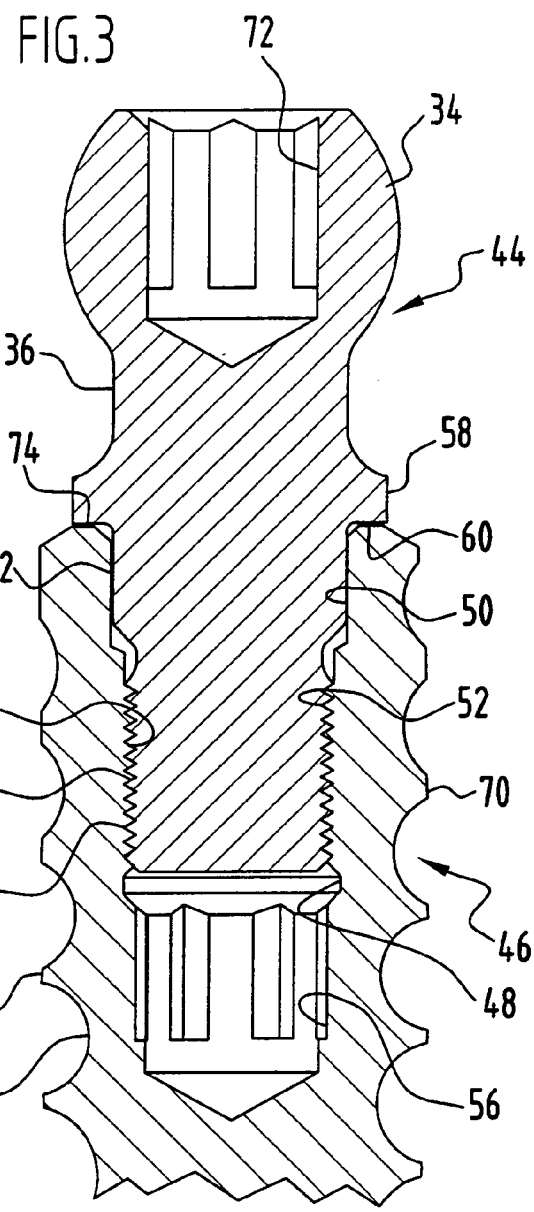
FIG. 3: a longitudinal sectional view through a proximal end region of the screw body of the bone screw illustrated in FIG. 2.

There now follows a detailed description of the construction of the bone screw 12 with reference to FIGS. 1 to 3. The bone screw 12 comprises two main parts, namely the screw head 24 and the screw body 28, which is connected thereto in articulated manner and defines a screw body longitudinal axis 30. The screw body 28 comprises a screw core 33, which on its proximal end bears a substantially spherical coupling head 34 that merges via a necking 36 into the screw body 28. The screw body 28 with its screw core 32 and the coupling head 34 is, as a whole, of a rotationally symmetrical construction. The screw core 32 on its outer side carries an external thread 38, which in the front third, i.e. adjacent to its distal end, which is designed as a screw point 40, comprises a self-cutting threaded portion 42.

The screw body 28 itself is separable into two parts, namely into a coupling part 44 comprising the coupling head 34 and into a threaded part 46 substantially comprising the screw core 32. The coupling part 44 is screw-fastenable to the threaded part 46. For this purpose, a proximal end of the threaded part 46 is provided coaxially with the screw body longitudinal axis 30 with a blind hole 48, which starting from the proximal end of the threaded part 46 is subdivided into three mutually adjoining portions. The proximal end of the coupling part 44 is directly adjoined by a hollow cylindrical portion 50. In distal direction of the portion 50, the diameter of the blind hole is reduced in a single stage and provided with an internal thread 54 on a coupling portion 52, which comprises approximately a third of the length of the blind hole 48. Adjoining the distal end of the coupling portion 50 is a tool element receiver in the form of a hexagon socket 56.

Distally adjoining the necking 36, the coupling part 44 has a radially outwardly projecting annular flange 58, which forms an annular stop face 60 facing in distal direction for an annular end edge 74 facing in proximal direction on the proximal end of the threaded part 46. The annular flange 58 is adjoined at the distal end by a cylindrical portion 62, the outside diameter of which corresponds to the inside diameter of the cylindrical portion 50, with the result that the cylindrical portion 62 may be introduced substantially positively into the cylindrical portion 50. The outside diameter of the coupling part 44 is reduced in a single stage at the distal end of the cylindrical portion 62 and forms a cylindrical screw bolt portion 64, which is provided with an external thread 66 corresponding to the internal thread 54. The internal thread 54 and the external thread 66 are designed in the form of a fine-pitch thread. The annular flange 58 is disposed approximately in the middle of the coupling part 44, i.e. the length of the cylindrical portion 62, which can be introduced into the threaded part 46, together with the screw bolt portion 64 is approximately as long as the coupling head 34 with necking 36 that extends from the proximal end of the annular flange 58 in the direction of the screw body longitudinal axis 30. The depth of the blind hole 48 in the bone screw 12 illustrated in FIGS. 1 to 3 is approximately 40% of the total length of the threaded part 46.

The threaded part 46 has a maximum outside diameter 68. The outside diameter 68 is defined by the external thread 38, which along approximately 60% of the length of the threaded part 46 has a constant outside diameter that corresponds to the outside diameter 68. The screw core 32, on the other hand, starting from the proximal end of the threaded part 46 is of a slightly conical shape and merges into a conical portion, which tapers to a greater extent in the direction of the distal end having the screw point 40 and which in turn merges into a short cylindrical portion, on which finally the screw point 40 is formed. The constant outside diameter 68 of the external thread 38 in conjunction with the decreasing diameter of the screw core 32 in the region of the conical portions thereof has the result that a width of the thread cutting edge 70 decreases monotonically from the proximal end of the threaded part 46.

To facilitate the screwing-together of coupling part 44 and threaded part 46, the coupling head 34 is provided coaxially with the screw body longitudinal axis 30 with a blind-hole-like hexagon socket 72, which is open in proximal direction. Providing the hexagon sockets 56 and 72 makes it possible, first, to screw the threaded part 46 into the vertebral body 20 by means of a non-illustrated screw-in tool provided with a hexagon insert bit. Then, by means of a further screw-in tool carrying a hexagon insert bit the coupling part 44 may be screw-fastened to the threaded part 46, namely until the stop face 60 abuts on the annular end edge 74 of the proximal end of the threaded part 46.

There now follows a detailed description of the construction of the screw head 24 with reference to FIG. 2. An elongate tubular sleeve 76 forms a basic body of the screw head 24 that defines a screw head longitudinal axis 78. For the articulated connection, i.e. for forming a ball-and-socket joint with the coupling head 34, a distal end of the sleeve 76 diminishes in inside diameter continuously and forms a short hollow spherical portion 80. An inside diameter of the sleeve 76, apart from the hollow spherical portion 80, corresponds approximately to the maximum outside diameter of the coupling head 34 in a direction transversely of the screw body longitudinal axis 30. In other words, the hollow spherical portion 80 thus forms an axial stop for the coupling head 34 for limiting a movement of the screw body 28 relative to the screw head 24 in distal direction.

Starting from a proximal end, the sleeve 76 is provided with two mutually diametrically opposed longitudinal slots 82, which extend over approximately 80% of a total length of the screw head 24 and define a plane containing the screw head longitudinal axis 78. The longitudinal slots 82 form two diametrically opposed, substantially half-shell-shaped, curved limbs 84 and 86, which project in proximal direction parallel to the screw head longitudinal axis 78, with the result that the screw head 24 assumes the shape of a fork head or tulip head. The sleeve 76 is provided approximately midway, in relation to the screw head longitudinal axis, along its outer side with an annular groove, which forms in the limbs 84 and 86 notches 88 and 90 respectively, which serve as predetermined breaking points for removal of a proximal half of the limbs 84 and 86.

In principle, it would be possible to insert the round rod 16 with its longitudinal axis 92 transversely of the screw head longitudinal axis 78 in the longitudinal slots 82 forming a connection element receiver. However, in order to achieve a particularly high surface pressure, a sleeve-shaped clamping part 94 is provided, which has an outside diameter adapted to the inside diameter of the sleeve 76 and has a distal end with a hollow spherical end edge 96, which corresponds to the coupling head 34, lies directly against the coupling head 34 and forms an axial stop for the coupling head 34 in proximal direction. The clamping part 94 at the proximal end is provided with two diametrically opposed recesses 98, the radius of which corresponds to the radius of the round rod 16, with the result that the round rod 16 may come into surface contact at a proximal edge of the clamping part 94 when the screw head longitudinal axis 78 and the longitudinal axis 92 intersect at right angles. It would in particular be conceivable to select a diameter of the round rod 16 that is slightly larger than a diameter of the recesses 98 in order to enable an interference fit of the two parts, so that during assembly the limbs 84 and 86 of the screw head 24 are spread slightly apart and, as soon as the round rod 16 is inserted into the recesses 98, the two parts are held securely on one another.

Adjacent to its distal end, the sleeve 76 is provided with a transverse bore 112. This forms part of a locking device for holding the clamping part 94 captive on the screw head 24. A further component of the locking device is a spring tongue 114 disposed on the clamping part 94 and projecting parallel to the screw head longitudinal axis 78, which spring tongue 114 forms part of the outer wall of the clamping part 94. Projecting radially outwards from the spring tongue 114 is a prism-shaped detent projection 116, which has a detent surface 118 facing in proximal direction transversely of the screw head longitudinal axis and a slide-on surface 120 inclined in distal direction obliquely relative to the screw head longitudinal axis 78.

For fixing the round rod 16 non-rotatably to the screw head 24 a tensioning screw 100 is provided, which has a central opening in the form of a hexagon socket 102 and is provided at its outer side with a tensioning screw thread 104, which corresponds to an internal thread 106 of the sleeve 76 that extends along approximately 40% of the length of the sleeve 76. The greater part of the internal thread 106 is provided at the proximal side of the notches 88 and 90. A portion of the internal thread 106 at the distal side of the notches 88 and 90, however, has a length that is slightly greater than a height of the tensioning screw 100 in the direction of the screw head longitudinal axis 78. It is thereby ensured that, after the proximal ends of the limbs 84 and 86 have been broken off, the tensioning screw 100 is disposed entirely in the interior of the screw head 24.

The outside diameter 68 of the threaded part 46 of the screw body 28 is larger than a minimum diameter 108 of the sleeve 76 that is defined by the hollow spherical portion 80 adjacent to the distal end of the sleeve 76. A maximum outside diameter of the coupling part 44 at the distal side of the annular flange of the screw body 28 is, on the other hand, smaller than the inside diameter 108. This allows the coupling part 44 to be pushed from the proximal side through a circular opening 110, which is delimited by the hollow spherical portion 80, until the coupling head 34 abuts on the hollow spherical portion 80. In this way, the screw head 24 is connectable to the screw body 28 even though the outside diameter 68 of the threaded part 46 is larger than the inside diameter 108 of the opening 110.

In order to insert the bone screw 12 into the vertebral body 20, firstly, as already described, the threaded part 46 is screwed into the vertebral body 20. Alternatively, the bone screw 12 is preassembled already at the time of manufacture, i.e. the distal end of the coupling part 44 is passed through the opening 110 of the screw head 24 and screw-fastened to the threaded part 46. In said case, it is ensured that a tightening torque is at least 5 Nm, preferably however not more than 20 Nm. In a preferred manner, approximately 10 Nm is provided as a tightening torque. After the bone screw 12 has been assembled under clean-room conditions, it is additionally γ-sterilized because the hexagon socket 56 forms a cavity, into which during assembly germs, bacteria or other impurities may penetrate. These are killed and/or eliminated by exposing the bone screw 12 to γ-radiation.

If the bone screw is not preassembled in the manner just described, in the next step the clamping part 94 is inserted from the proximal side into the screw head 24. In said case, the slide-on surface 120 of the spring tongue 114 slides along an inner wall of the sleeve-shaped screw head 24 until the detent projection 116 engages into the transverse bore 112. A movement of the clamping part 94 in proximal direction is therefore no longer possible because the detent surface 118 limits a movement in proximal direction by abutting on the transverse bore 112. A separating of the clamping part 94 from the screw head 24 is possible only if the spring tongue 114 is pressed in the direction of the screw head longitudinal axis 78 and at the same time the clamping part 94 is moved in proximal direction. In any case, by inserting of the clamping part 94 into the screw head 24, the screw head 24 is held captive on the coupling part 44. Whilst the screw head 24 is able to move relative to the coupling part 44, the screw head 24 is no longer able to detach from the coupling part 44.

In a next step, the coupling part 44 connected to the screw head 24 is screw-fastened to the threaded part 46 in the manner already described above.

In principle, the tensioning screw 100 might be screw-fastened to the screw head 24 directly after insertion of the clamping part 44. Then, however, the round rod 16 has to be pushed laterally into the recesses 98 of the screw head 24. Alternatively, it is also possible, first, to introduce the round rod 16 parallel to the screw head longitudinal axis 78 into the screw head 24 and bring it into contact with the recess 98 and, only then, insert the tensioning screw 100. After insertion of the tensioning screw 100, the round rod 16 is roughly locked against falling out of, or separating from, the bone screw 12.

In a next step, the final position of the screw head 24 relative to the screw body 28 may be adjusted. Once this position has been found, the tensioning screw 100 is tightened, with the result that the round rod 16 is held clamped between the tensioning screw 100 and the clamping part 94. At the same time, by means of the tensioning screw 100 via the round rod 16 and the clamping part 94 the coupling head 34 is also loaded against the hollow spherical portion 80. In this way, the round rod 16 is fixable on the screw head 24 and the screw head 24 is in turn fixable immovably on the screw body 28.

As already mentioned initially, the screw head 26 of the bone screw 14 corresponds to the screw head 24 of the bone screw 12. The bone screw 12 and the bone screw 14 differ from one another in that, in the case of the bone screw 14, an, on the whole, integral screw body 122 is provided, the maximum outside diameter 124 of which is smaller than an inside diameter 128 of an opening 126 of the screw head 26 that corresponds to the opening 110. This means that the screw body 26 does not have to be split up like the screw body 28 in order to connect the screw body 122 to the screw head 26, as is the case with the bone screw 12.

To insert the bone screw 14, first, as in the case of the bone screw 12, the screw body 122 is inserted, but in the case of the bone screw 14 as a whole, through the opening 126 and then the clamping part 94 (not shown in detail) is inserted in order to secure the screw head 26 on the screw body 122. The further procedure for insertion of the bone screw 14 corresponds to that for insertion of the bone screw 12.

What is claimed is:

1. A bone screw, comprising:
   a screw head having a U-shaped fork head with a coupling opening,
   a preassembled screw body comprising at least a first and a second screw body part which are connected to one another with a tightening torque which is greater than a release torque required to remove the bone screw from a bone, said screw body defining a longitudinal axis and being provided with a screw body external thread and having a proximal end and a distal end,
   a coupling element formed on the proximal end of the screw body for detachably connecting the screw body to the screw head,
   wherein:
   an edge of the coupling opening forms an axial stop for the coupling element for limiting a movement of the coupling element relative to the screw head in a distal direction,
   a maximum outside diameter of the screw body is larger than an inside diameter of the coupling opening,
   the coupling element is disposed on a proximal end of the first screw body part and the second screw body part carries the external thread of the screw body,
   the first screw body part has a first connection element for a detachable connection to a second connection element disposed on the second screw body part,
   the first screw body part has a distal end, which can be introduced in the distal direction through the coupling opening and which comprises the first connection element;
   the second connection element comprises an internal connection element thread,
   the first connection element comprises an external connection element thread corresponding to the internal connection element thread, and
   the internal connection element thread and the external connection element thread are disposed coaxially with the longitudinal axis of the screw body.

2. A bone screw according to claim 1, wherein the screw head and the coupling element in a connection position, in which the screw head is connected to the screw body, are connected to one another in an articulated manner.

3. A bone screw according to claim 1, wherein the coupling element is spherical.

4. A bone screw according to claim 1, wherein the internal connection element thread and the external connection element thread are fine-pitch threads.

5. A bone screw according to claim 1, wherein the coupling opening has an inside diameter that is smaller than an outside diameter of the coupling element.

6. A bone screw according to claim 1, wherein:
   the fork head comprises a connection element receiver, which is delimited by two limbs projecting in a proximal direction, and
   a carrier element of an osteosynthesis device for connecting two bone screws can be inserted into the connection element receiver and fastened in the connection element receiver.

7. A bone screw according to claim 6, wherein at least one of the two limbs of the fork head has a predetermined breaking point.

8. A bone screw according to claim 6, wherein at least one fixing means is provided for fixing the carrier element in the connection element receiver.

9. A bone screw according to claim 8, wherein the fixing means is screw-fastenable to the screw head.

10. A bone screw according to claim 8, wherein the fork head has a fork head thread and the fixing means has a fixing means thread corresponding to the fork head thread.

11. A bone screw according to claim 10, wherein the fixing means thread is an external thread and the fork head thread is an internal thread.

12. A bone screw according to claim 10, wherein the fixing means thread and the fork head thread are formed coaxially with a screw head longitudinal axis.

13. A bone screw according to claim 1, wherein the fork head is formed from an elongate fork head sleeve, which starting from its proximal end is provided with two diametrically opposed slots, which form a connection element receiver, so that a distal end of the fork head is designed in the form of an annular sleeve portion comprising the coupling opening.

14. A bone screw according to claim 1, wherein the first screw body part carries a first tool element receiver for a tool for connecting the first screw body part to the second screw body part.

15. A bone screw according to claim 14, wherein the first tool element receiver is disposed on the coupling element facing in a proximal direction.

16. A bone screw according to claim 14, wherein the first tool element receiver is designed in the form of a slot.

17. A bone screw according to claim 1, wherein the second screw body part carries a second tool element receiver for a screw-in tool for screwing the second screw body part into the bone.

18. A bone screw according to claim 1, wherein:
there is provided a clamping body supported movably on the fork head, and
the clamping body can be clamped against the coupling element.

19. A bone screw according to claim 18, wherein a locking device is provided for detachably connecting the clamping body to the screw head.

20. A bone screw according to claim 18, wherein a carrier element of an osteosynthesis device for connecting two bone screws can be inserted into a connection element receiver and held between a fixing element and the clamping body.

21. A bone screw according to claim 20, wherein the carrier element is rod-shaped.

22. A bone screw according to claim 1, wherein the first screw body part has a stop, on which the second screw body part abuts when the two screw body parts are connected to one another.

23. A bone screw according to claim 22, wherein the stop is designed in the form of a radially projecting annular flange.

24. A bone screw according to claim 22, wherein a spacing of the distal end of the first screw body part from the stop corresponds at most to 0.4 times a total length of the second screw body part.

25. A bone screw according to claim 1, wherein the screw head defines a screw head longitudinal axis and a plane of symmetry of a connection element receiver contains the screw head longitudinal axis.

26. A bone screw according to claim 1, wherein the screw body has a core, which comprises at least one cylindrical and two conical portions.

27. A bone screw according to claim 26, wherein a first conical portion of the core adjoins the proximal end of the screw body, that the first conical portion merges into a second conical portion, that the second conical portion merges into a cylindrical portion and that the cylindrical portion merges into a screw body point.

28. A bone screw according to claim 1, wherein the first and the second connection element have a diameter corresponding at most to 0.7 times the mean diameter of a core of the screw body in a portion of the screw body in which one of the two connection elements is provided.

29. A bone screw according to claim 1, wherein an outside diameter of the external thread of the screw body is constant over at least half of a length of the screw body.

30. A bone screw according to claim 1, wherein the defined tightening torque is in the range of 5 to 20 Nm.

31. A bone screw according to claim 30, wherein the tightening torque is approximately 10 Nm.

32. A bone screw according to claim 1, wherein the screw head and the first and the second screw body part are connected under clean-room conditions.

33. A bone screw according to claim 1, wherein, after the connection of screw head and first and second screw body part, the bone screw is sterilized.

34. A bone screw according to claim 33, wherein the bone screw is sterilized by exposure to γ-radiation.

35. An osteosynthesis device for fixing at least two bone parts relative to one another in a fixation position, comprising:
at least two bone screws, and
a carrier element which can be fastened to at least two of the at least two bone screws,
at least one of the at least two bone screws is a bone screw comprising:
a screw head having a U-shaped fork head with a coupling opening,
a preassembled screw body comprising at least a first and a second screw body part which are connected to one another with a tightening torque which is greater than a release torque required to remove the bone screw from a bone, said screw body defining a longitudinal axis and being provided with a screw body external thread and having a proximal end and a distal end,
a coupling element disposed on the proximal end for detachably connecting the screw body to the screw head,
wherein:
an edge of the coupling opening forms an axial stop for the coupling element for limiting a movement of the coupling element relative to the screw head in a distal direction,
a maximum outside diameter of the screw body is larger than an inside diameter of the coupling opening,
the coupling element is formed on a proximal end of the first screw body part and the second screw body part carries the external thread of the screw body,
the first screw body part has a first connection element for a detachable connection to a second connection element disposed on the second screw body part, and
the first screw body part has a distal end, which can be introduced in the distal direction through the coupling opening and which comprises the first connection element;

the second connection element comprises an internal connection element thread, the first connection element comprises an external connection element thread corresponding to the internal connection element thread, and the internal connection element thread and the external connection element thread are disposed coaxially with the longitudinal axis of the screw body.

36. An osteosynthesis device according to claim 35, wherein the osteosynthesis device comprises at least one bone screw which has a screw body formed as piece with an outside diameter that is smaller than an inside diameter of a coupling opening of a screw head connectable to the screw body, so that for the assembly of the bone screw the screw body can be passed in the distal direction through the coupling opening.

37. An osteosynthesis device according to claim 35, wherein the carrier element fixed in a connection element receiver completely covers the coupling opening in an axial direction.

* * * * *

UNITED STATES PATENT AND TRADEMARK OFFICE
CERTIFICATE OF CORRECTION

| | | |
|---|---|---|
| PATENT NO. | : 7,717,942 B2 | Page 1 of 1 |
| APPLICATION NO. | : 11/138771 | |
| DATED | : May 18, 2010 | |
| INVENTOR(S) | : J. Schumacher | |

It is certified that error appears in the above-identified patent and that said Letters Patent is hereby corrected as shown below:

Column 16, line 1, claim 36 is corrected to read: --screw which has a screw body formed as one-piece with an outside--

Signed and Sealed this

Thirteenth Day of July, 2010

David J. Kappos
*Director of the United States Patent and Trademark Office*